United States Patent [19]

Carson

[11] 4,255,335

[45] Mar. 10, 1981

[54] PREPARATION OF 5-AROYL-1-LOWERALKYLPYRROLE-2-ACETIC ACID DERIVATIVES

[75] Inventor: John R. Carson, Norristown, Pa.

[73] Assignee: McNeilab, Inc., Fort Washington, Pa.

[21] Appl. No.: 137,046

[22] Filed: Apr. 3, 1980

[51] Int. Cl.$^3$ .......................................... C07D 207/337
[52] U.S. Cl. ............................ 260/326.47; 260/326.62; 260/326.5 J
[58] Field of Search ........................ 260/326.47, 326.62, 260/326.5 J

[56] References Cited

U.S. PATENT DOCUMENTS

| | | | |
|---|---|---|---|
| 3,752,826 | 8/1973 | Carson | 260/326.46 |
| 3,957,818 | 5/1976 | Carson | 260/326.62 |
| 3,998,844 | 12/1976 | Carson | 260/326.47 |
| 4,119,639 | 10/1978 | Carson | 260/326.47 |
| 4,194,003 | 3/1980 | La Forest et al. | 260/326.47 |
| 4,207,237 | 6/1980 | Carson et al. | 260/326.47 |

*Primary Examiner*—Mary C. Lee

[57] ABSTRACT

Known types of 5-aroyl-1-loweralkylpyrrole-2-acetic acid derivatives are prepared by the thermal reaction of an aroylcyanide with a 1-alkylpyrrole-2-acetic acid derivative.

3 Claims, No Drawings

PREPARATION OF 5-AROYL-1-LOWERALKYLPYRROLE-2-ACETIC ACID DERIVATIVES

5-Aroyl-1-loweralkylpyrrole-2-acetic acid derivatives (III) are prepared by the following new process: an aroylcyanide (I) is caused to react with an 1-alkylpyrrole-2-acetic acid derivative (II) at elevated temperatures to give, after the loss of the elements of hydrogen cyanide, a 5-aroyl-1-loweralkylpyrrole-2-acetic acid derivative (III). Compounds of type III are known and useful as intermediates to 5-aroyl-1-loweralkylpyrrole-2-acetic acid anti-inflammatory agents (IV) (Carson, U.S. Pat. No. 3,752,826). The reaction is as set forth in the following schematic diagram:

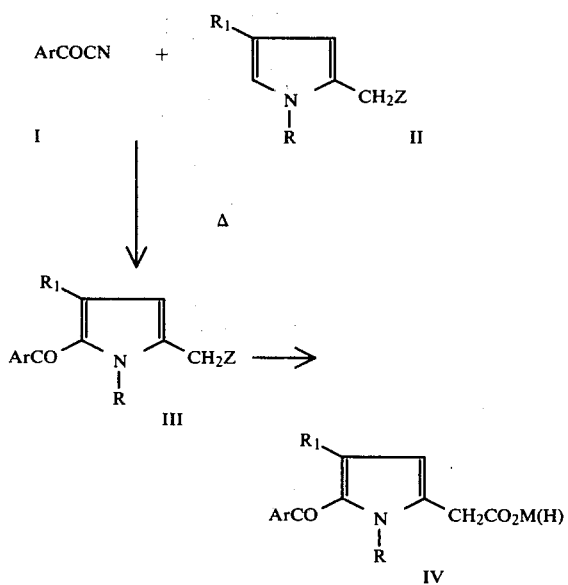

wherein:
Ar represents phenyl or phenyl substituted by a member selected from the group consisting of loweralkyl, halo, nitro, methylthio, trifluoromethyl, and loweralkoxy;
R represents loweralkyl;
$R_1$ represents hydrogen or lower alkyl;
Z represents —CN or —$CO_2$ loweralkyl;
M represents alkali metal, for example Na, K.

As used herein, "loweralkyl" and "loweralkoxy" may be straight or branch chained saturated hydrocarbons having from one to six carbon atoms, such as, for example, methyl, ethyl, propyl, isopropyl, butyl, pentyl, hexyl, and the like alkyls, and respectively, the corresponding alkoxys such as methoxy, ethoxy, propoxy, isopropoxy, etc.

ADVANTAGES OF THE PRESENT INVENTION

The process of the present invention has advantages over prior art methods. The Friedel Crafts aroylation of 1-loweralkylpyrrole-2-acetic acid derivative produces a mixture of 4- and 5-aroyl-1-loweralkylpyrrole-2-acetic acid derivatives [J. R. Carson, S. Wong, and D. S. McKinstry, J. Med. Chem., 14, 647 (1971)]. The process of the present invention, however, produces only the 5-aroyl isomer. The uncatalyzed reaction of aroylhalides with 1-loweralkylpyrrole-2-acetic acid derivatives (Carson, U.S. Pat. No. 3,998,844) produces a stoichiometric quantity of a hydrogen halide. The presence of a strong acid can induce polymerization of pyrroles [Advances in Heterocyclic Chemistry, ed. Katritsky, Vol. 2, p. 287, Academic Press, N.Y. (1963)].

The process of the present invention does not produce a strong acid. The process of the present invention is preferably carried out without solvent. Thus, a high ratio of product to reactor volume is obtained.

UTILITY

Compounds of type III are useful as intermediates to 5-aroyl-1-loweralkylpyrrole-2-acetic acids (IV) and their salts. The hydrolytic conversion of intermediates of type III to products of type IV is disclosed in U.S. Pat. No. 3,752,826. Agents of type IV are useful as anti-inflammatories and analgesics. Well-known agents of type IV include tolmetin sodium dihydrate, i.e., sodium 1-methyl-5-p-toluoylpyrrole-2-acetate dihydrate and zomepirac sodium dihydrate, i.e., sodium 5-(4-chlorobenzoyl)-1,4-dimethylpyrrole-2-acetate dihydrate among the better known members of this class of compounds.

DETAILED DESCRIPTION

The process of the present invention is carried out by heating an aroylcyanide (I) with a 1-loweralkylpyrrole-2-acetic derivative (II) at a temperature in the 100°–250° range, preferably at 120°–180°. It is preferably carried out in the absence of any solvent, but, if desired, it can be carried out in the presence of a high boiling aprotic inert solvent such as xylene, p-cymeme or o-dichlorobenzene. The reaction preferably is carried out while passing a stream of inert gas, such as nitrogen, through the mixture. The product III may be purified or used without further purification in conversion to IV.

PREPARATION OF STARTING MATERIALS

The aroylcyanides used as starting materials for the present invention are known compounds or classes of compounds. Thus, those aroylcyanides (I) wherein Ar is phenyl or phenyl substituted by loweralkyl, halo, and loweralkoxy are disclosed in Koenig & Weber, Tet. Let., 2275 (1974). While that article only teaches individual compounds other members of the class may be made in the same manner there described. Those aroylcyanide (I) compounds wherein Ar is nitrophenyl are disclosed in Normant & Piechucki, Bull. Soc. Chem. France, 2402 (1972). The aroylcyanide compounds wherein Ar represent trifluoromethylphenyl and methylthiophenyl are not known, but can be made by the procedure taught by Normant & Piechucki above, i.e., by reacting p-methylthiobenzoyl chloride or m-trifluoromethylbenzoyl chloride, with copper cyanide in the presence of methylcyanide, the desired aroylcyanide products will be obtained.

The loweralkylpyrrole-2-acetic acid derivatives (II) wherein Z represents $CO_2$alkyl are known compounds, as disclosed in U.S. Pat. No. 3,752,826 in Examples CXI and CXXI. Those compounds in (II), wherein Z represents CN, are disclosed in U.S. Pat. No. 3,957,818.

In the following Examples, which are intended to illustrate the invention but not to limit it, all temperatures are in degrees Celsius (°C.).

EXAMPLE I(A)

Methyl 1-methyl-5-(4-methylbenzoyl)pyrrole-2-acetate

A mixture of 5.0 g (0.034 mole) of 4-methylbenzoylcyanide and 0.8 g (0.005 mole) of methyl 1-methyl-pyrrole-2-acetate was added over 4 hours from a heated addition funnel to a sample of 3.8 g (0.025 mole) of methyl 1-methylpyrrole-2-acetate at 180° through which nitrogen was bubbled. The mixture was heated for six more hours after the addition was complete. The reaction was cooled and dissolved in methylene chloride-toluene. The organic solution was washed with 10 percent sodium hydroxide solution and saturated brine and dried ($MgSO_4$). The solvent was evaporated in vacuo and the residue recrystallized twice from methanol to give 5.41 g (69 percent yield) of white crystalline methyl 1-methyl-5-(4-methyl-benzoyl)-pyrrole-2-acetate, mp 118°–120° C. The solid state IR spectrum was identical to authentic material.

EXAMPLE I(B)

Following the procedure of Example I(A), but replacing the 4-methylbenzoylcyanide with each of the following:
3-propylbenzoylcyanide;
4-methoxybenzoylcyanide;
4-nitrobenzoylcyanide;
4-methylthiobenzoylcyanide;
3-trifluoromethylbenzoylcyanide
there can be obtained the following, respectively:
methyl 1-methyl-5-(3-propylbenzoyl)pyrrole-2-acetate;
methyl 1-methyl-5-(4-methoxybenzoyl)pyrrole-2-acetate;
methyl 1-methyl-5-(4-nitrobenzoyl)pyrrole-2-acetate;
methyl 1-methyl-5-(4-methylthiobenzoyl)pyrrole-2-acetate;
methyl 1-methyl-5-(3-trifluoromethylbenzoyl)pyrrole-2acetate.

EXAMPLE II(A)

Ethyl 5-(4-chlorobenzoyl)-1,4-dimethylpyrrole-2-acetate

A 1.50 g (0.0090 mole) sample of 4-chlorobenzoylcyanide was added over a one-hour period to 1.50 g (0.0082 mole) of ethyl 1,4-dimethylpyrrole-2-acetate at 120°–130° through which nitrogen was slowly bubbled. The mixture was heated for 27 hours. The resulting oil was chromatographed on silica gel with successive elution with hexane and 1,1,1-trichloroethane. The solvent was evaporated in vacuo from compound-bearing fractions. The residue was chromatographed through a Waters Associates, Prep LC, System 500 with elution with a 2:3 mixture of hexane:1,1,1-trichloroethane. Evaporation of solvent from the second compound-bearing fraction afforded solid which was recrystallized from methanol to give 0.74 g (28 percent yield) of ethyl 5-(4-chlorobenzoyl)-1,4-dimethylpyrrole-2-acetate, mp 108°–109°, undepressed by admixture with authentic material.

EXAMPLE II(B)

Following the procedure of Example II(A), but replacing the ethyl 1,4-dimethylpyrrole-2-acetate with each of the following:
ethyl 1,4-diethylpyrrole-2-acetate;
methyl 1-methyl-4-ethylpyrrole-2-acetate,
there can be obtained the following, respectively:
ethyl 5-(4-chlorobenzoyl)-1,4-diethylpyrrole-2-acetate;
methyl 5-(4-chlorobenzoyl)-1-methyl-4-ethylpyrrole-2-acetate.

EXAMPLE III(A)

Sodium 1-methyl-5-(4-methylbenzoyl)pyrrole-2-acetate dihydrate

A mixture of 7.0 g (0.042 mole) of ethyl 1-methylpyrrole-2-acetate and 7.25 g (0.05 mole) of 4-methylbenzoylcyanide was heated at 180° for 24 hours.

The mixture was dissolved in ether. The solution was washed with dilute sodium hydroxide solution and saturated brine. The solution was dried ($MgSO_4$). The solvent was evaporated in vacuo.

The residue was heated under reflux with 100 ml of 25 percent sodium hydroxide for one hour. The mixture was cooled and the precipitated solid was collected by filtration and washed with cold ethanol. The solid was recrystallized from ethanol with removal of insoluble material by hot filtration. Two crops of crystals were taken totalling 8.23 g. This was recrystallized from ethanol to give 6.11 g (46 percent yield) of sodium 1-methyl-5-(4-methylbenzoyl)pyrrole-2-acetate dihydrate, mp 298°–300°. The solid state infrared spectrum was indentical to authentic material.

EXAMPLE III(B)

Following the procedure of Example III(A), but replacing the 4-methylbenzoylcyanide with each of the following aroylcyanides:
3-propylbenzoylcyanide;
4-methoxybenzoylcyanide;
4-bromobenzoylcyanide;
4-nitrobenzoylcyanide;
4-methylthiobenzoylcyanide;
3-trifluoromethylbenzoylcyanide,
there can be obtained the following, respectively:
sodium 1-methyl-5-(3-propylbenzoyl)pyrrole-2-acetate dihydrate;
sodium 1-methyl-5-(4-methoxybenzoyl)pyrrole-2-acetate dihydrate;
sodium 1-methyl-5-(4-bromobenzoyl)pyrrole-2-acetate dihydrate;
sodium 1-methyl-5-(4-nitrobenzoyl)pyrrole-2-acetate dihydrate;
sodium 1-methyl-5-(4-methylthiobenzoyl)pyrrole-2-acetate dihydrate;
sodium 1-methyl-5-(3-trifluoromethylbenzoyl)pyrrole-2-acetate dihydrate.

EXAMPLE IV

1-Methyl-5-(4-methylbenzoyl)pyrrole-2-acetonitrile

A mixture of 2.1 g (0.018 mole) of 1-methylpyrrole-2-acetonitrile and 5.0 g (0.035 mole) of 4-methylbenzoyl cyanide was added dropwise over six hours to a sample of 4.1 g (0.034 mole) of 1-methylpyrrole-2-acetonitrile at 180° through which a stream of nitrogen was passed. The mixture was heated a total of two days at 180°. It was cooled, dissolved in $CHCl_3$, washed with 10 percent NaOH solution, dried ($MgSO_4$) and the solvent evaporated in vacuo to give 10.1 g of a black oil. The oil was triturated with ether. The ether was decanted from tarry material and charcoaled. The ether was evaporated in vacuo to give 7.4 g of oil. The excess 1-methyl-pyrrole-2-acetonitrile was removed by distillation in a Kugelrohr apparatus at 70° C., 0.1 mm/Hg. The residue (4.2 g) was chromatographed on a Waters Associate System 500 preparative hplc. using ethyl acetate:cyclohexane, 1:3 as eluant and two passes through the column. The fractions corresponding on TLC to desired product were evaporated in vacuo to give 1.1 g of an oil. The oil was triturated with cyclohexane and the cyclohexane was decanted and evaporated in vacuo. The residue was recrystallized from methanol to give 30 mg of 1-methyl-5-(4-methylbenzoylpyrrole-2-acetonitrile), m.p. 101°–105° C., undepressed upon admixture with authentic material. The solid state IR was identical to that from authentic material.

I claim:

1. The process of preparing 5-aroyl-1-loweralkylpyrrole-2-acetic acid derivatives of formula:

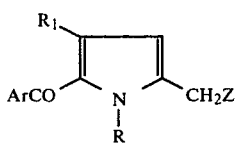

which comprises reacting an aroylcyanide of formula: ArCOCN with a 1-loweralkylpyrrole-2-acetic acid derivative of the formula:

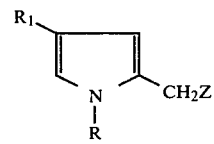

said reaction being carried out by heating at a temperature above 100° C., wherein in the foregoing formulae:
R is loweralkyl;
$R_1$ is hydrogen or loweralkyl;
Ar is phenyl or phenyl substituted with a substituent selected from the group consisting of loweralkyl, halo, nitro, methylthio, trifluoromethyl and alkoxy;
Z is —CN or —$CO_2$ loweralkyl.

2. The process of claim 1, wherein 4-methylbenzoylcyanide is reacted with methyl 1-methylpyrrole-2-acetate to produce methyl 1-methyl-5-(4-methylbenzoyl)-pyrrole-2-acetate.

3. The process of claim 1, wherein 4-chlorobenzoylcyanide is reacted with ethyl 1,4-dimethylpyrrole-2-acetate to produce ethyl 5-(4-chlorobenzoyl)-1,4-dimethyl-pyrrole-2-acetate.

* * * * *